United States Patent [19]

Shuman et al.

[11] Patent Number: 5,039,814

[45] Date of Patent: Aug. 13, 1991

[54] ORTHO-LITHIATION PROCESS FOR THE SYNTHESIS OF 2-SUBSTITUTED 1-(TETRAZOL-5-YL)BENZENES

[75] Inventors: Richard F. Shuman, Westfield; Anthony O. King, Hillsborough; Robert K. Anderson, Plainsboro, all of N.J.

[73] Assignee: Merck & Co., Inc., Rahway, N.J.

[21] Appl. No.: 517,889

[22] Filed: May 2, 1990

[51] Int. Cl.$^5$ .................. C07D 257/02; C07F 3/00; C07F 5/00; C07F 1/00

[52] U.S. Cl. .................................. 548/250; 548/101; 548/110; 548/109

[58] Field of Search ............... 548/250, 101, 109, 110

[56] References Cited

U.S. PATENT DOCUMENTS 3,534,113 10/1970 Eastham et al.

4,870,186 9/1989 Aldrich et al. ................. 548/211

FOREIGN PATENT DOCUMENTS 0324377 7/1989 European Pat. Off. .

Primary Examiner—David B. Springer
Attorney, Agent, or Firm—Joseph F. DiPrima; William H. Nicholson; Salvatore C. Mitri

[57] ABSTRACT

A process utilizes the tetrazole functional group to direct lithiation at the ortho position of a phenyltetrazole and generate a nucleophilic aryllithium species which then undergoes reaction with an electrophile to generate a 2-substituted 1-(tetrazol-5-yl)benzene. The process is useful in the production of intermediates in the synthesis of angiotensin II antagonists. This novel process is a more cost effective and versatile route for the large-scale preparation of these key intermediates.

26 Claims, No Drawings

ORTHO-LITHIATION PROCESS FOR THE SYNTHESIS OF 2-SUBSTITUTED 1-(TETRAZOL-5-YL)BENZENES

BACKGROUND OF THE INVENTION

The renin-angiotensin system (RAS) plays a central role in the regulation of normal blood pressure and seems to be critically involved in hypertension development and maintenance as well as in congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of angioitensin II (A II) are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr., *Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; and 4,582,847; and 4,880,804 in European Patent Application Nos. 028,834; 245,637; 253,310; 323,841; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the cited references disclose compounds containing substituted imidazole and triazole compounds, which are generally bonded through a lower alkyl bridge to a substituted phenyl and preferably a biphenyl moiety containing a carboxylic acid or an acid equivalent. European Patent Application No. 245,637 discloses derivatives of 4,5,6,7-tetrahydro-2H-imidazol-[4,5-c]pyridine-6-carboxylic acid and analogs thereof as antihypertensive agents.

The process previously used in the synthesis of 1-(tetrazol-5-yl)-2-(4-tolyl)benzene entailed the cross-coupling of p-tolylzinc chloride and 1-cyano-2-bromobenzene, the biphenyl adduct is then converted to the tetrazole with ammonium azide (Finnegan, et al., *J. Am. Chem. Soc.*, 80, 3908–11, 1958.) or trimethyltin azide (Aldrich, et al., U.S. Pat. No. 4,870,186) to give the product 1-(tetrazol-5-yl)-2-(4-tolyl)benzene. The ammonium azide procedure requires long reaction times and produces low yields of the desired material. Prior to this invention, the preferred procedure required the use of trimethylstannyl chloride to generate the trimethylstannyl azide followed by reaction with the biphenyl adduct to give the desired tetrazole and the corresponding tin by-products. The disposal of these by-products is costly and coupled with the toxicity of tin make this route commercially unattractive.

These problems can be circumvented by the present invention which employs the reverse sequence of steps. The ortho-lithiation procedure is performed on (tetrazol-5-yl)benzene which is readily available from benzonitrile and ammonium azide (Finnegan, et. al.), or its N-trityl protected derivative, in high yields. The novel ortho-lithiation procedure allows for the preparation of the desired 1-(tetrazol-5-yl)-2-(4-tolyl)benzene through a more versatile and cost effective method.

DETAILED DESCRIPTION OF THE INVENTION

The novel process of this invention comprises as a first step the treatment of a (tetrazol-5-yl)benzene or an N-trityl protected derivative with a straight or branched ($C_1$–$C_6$)-alkyllithium in an aprotic solvent at a temperature of between $-40°$ and $10°$ C. and for a reaction time ranging between 30 minutes and 5 hours. The lithiation of the (tetrazol-5-yl)benzene is directed by the tetrazole substituent to lithiate the benzene ring at the ortho position, Scheme 1. The alkyllithium reagents preferably are n-butyllithium, sec-butyllithium and t-buytllithium; the preferred aprotic solvents are tetrahydrofuran, 2-methyltetrahydrofuran or diethyl ether; the preferred reaction time is between 30 minutes and 2 hours; and the preferred reaction temperature is between $-20°$ to $0°$ C.

The second step of the process comprises reacting the ortho-lithiated intermediate either directly, or after transmetallation with an electrophile, Scheme 2. The reaction mixture containing the ortho-lithiated intermediate is cooled to $-78°$ to $-60°$ C. and the electrophile, $E_1$, is added slowly. The reaction time ranges between 10 minutes and 5 hours and the reaction temperature ranges between $-78°$ to $25°$ C. Alternatively, the ortho-lithiated intermediate reacts with a metal halide, where the metal is selected from the group consisting of Zn, Mg, Cu, B, Al, and Cd, to give the transmetallated intermediate which then reacts with an electrophile, $E_2$, either in the presence or absence of a phosphinated nickel or palladium catalyst activated, when necessary, by a Grignard or an aluminum hydride reagent at a reaction temperature of between $-40°$ and $79°$ C. for a reaction time of 30 minutes to 16 hours to give the desired ortho-substituted product. This two-step process decreases the processing time and improves the yield of the product, such as 1-(2-trityltetrazol-5-yl)-2-(4-tolyl)benzene.

The more preferred process is the generation of an aryllithium by treating the protected or unprotected form of the tetrazole with n-butyllithium at $-20°$ to $-10°$ C. for between 30 minutes to 2 hours in tetrahydrofuran, 2-methyltetrahydrofuran or diethyl ether. The aryllithium intermediate is then reacted with zinc chloride in tetrahydrofuran while maintaining the temperature between $-10°$ and $0°$ C. The nickel catalyst, $(PPh_3)_2NiCl_2$, and the electrophile, p-iodotoluene, in tetrahydrofuran at $0°$ C. is activated with methylmagnesium chloride. The activated catalyst solution is added to the transmetallated product, arylzinc chloride, and maintaining the reaction temperature between $20°$ and $25°$ C. for a reaction time of between 30 minutes and 16 hours.

Scheme 1 illustrates the ortho-lithiation of the protected and unprotected aryltetrazole species to give the ortho-lithiated products B and A, respectively. Scheme 2 illustrates the versatility of the aryllithium species, showing the addition of the electrophile directly to the aryllithium, as well as the ability to transmetallate and then alkylate or arylate with the appropriate electrophile in the presence or absence of a catalyst.

Scheme 1

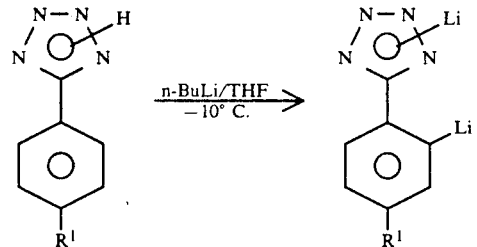

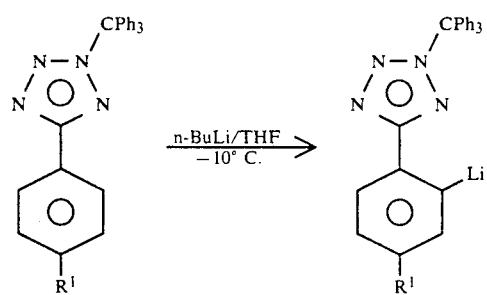

Scheme 2

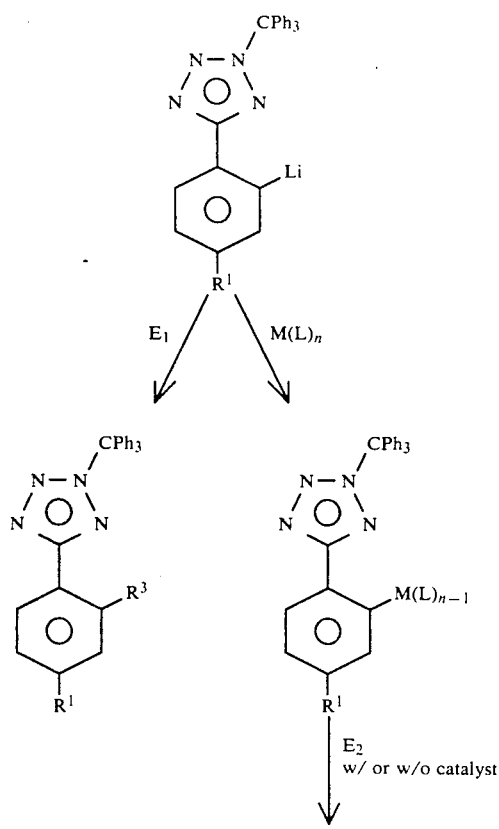

Scheme 2 -continued

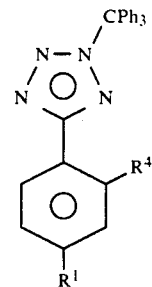

A

B

B $R^1$ is:
hydrogen,
t-butyl,
phenoxy,
phenyl,
di($C_1$-$C_6$)alkylamino, or
trimethylsilyl;

$R^2$ is:
hydrogen, or
trityl;

$E_1$ is:
benzaldehyde,
trimethylsilyl chloride,
phenyl disulfide,
methyl disulfide,
carbon dioxide,
ethylene oxide,
tosyl azide,
trimethylstannyl chloride,
($C_1$-$C_6$)-alkyl iodide,
iodine, or
bromine;

$R^3$ is:
α-hydroxybenzyl,
trimethylsilyl,
thiophenyl,
thiomethyl,
carboxyl,
2-hydroxyethyl,
azide,
trimethylstannyl,
($C_1$-$C_6$)-alkyl,
iodide, or
bromide, respectively;

$E_2$ is:
benzaldehyde,
($C_1$-$C_6$)alkanal,
($C_1$-$C_6$)-alkyl halide, wherein halide is Br, Cl, or I,
aryl halide, wherein aryl is defined as phenyl or phenyl substituted with o-, m- or p-($C_1$-$C_6$)-alkyl, o,p-di($C_1$-$C_6$)-alkyl, o-, m- or p-($C_1$-$C_6$)-alkoxyl, m- or p-phenyl, o-, m- or p-cyanol, m- or p-[carboxy-($C_1$-$C_6$)-alkyl], m- or p-nitro, o-, m- or p-chloro and the halide is Br or I,
bromine,
iodine, or
3-bromopropene;

$R^4$ is:
α-hydroxybenzyl,
α-hydroxy-($C_1$-$C_6$)-alkyl,
($C_1$-$C_6$)-alkyl,
phenyl,
o-, m- or p-($C_1$-$C_6$)-alkylphenyl, o,p-di($C_1$–$C_6$)-alkylphenyl,
o-, m- or p-($C_1$–$C_6$)-alkoxyphenyl,
3- or 4-biphenyl,
o-, m- or p-cyanophenyl,
m- or p-[carboxy-($C_1$–$C_6$)-alkyl]phenyl,
p- or m-nitrophenyl,
o-, m- or p-chlorophenyl,
bromide,
iodide, or
2-propen-1-yl, respectively;

M is:
  Zn,
  Mg,
  Cu,
  B,
  Al, or
  Cd;
L is:
  Cl,
  Br, or
  I;
n is:
  1,
  2, or
  3; and
the catalyst is:
  phosphinated Ni and Pd complexes such as $NiL_2(PPh_3)_2$, $PdL_2(PPh_3)_2$, or $Pd(PPh_3)_4$, wherein L is as defined above.

The preferred route used in the preparation of 1-(2-trityltetrazol-5-yl)-2-(4-tolyl)benzene is illustrated in Scheme 3 and which employs the ortho-lithiation of (2-trityltetrazol-5-yl)benzene, followed by transmetallation of the lithiated species and cross-coupling with 4-iodotoluene in the presence of a phosphinated nickel catalyst activated by $CH_3MgCl$.

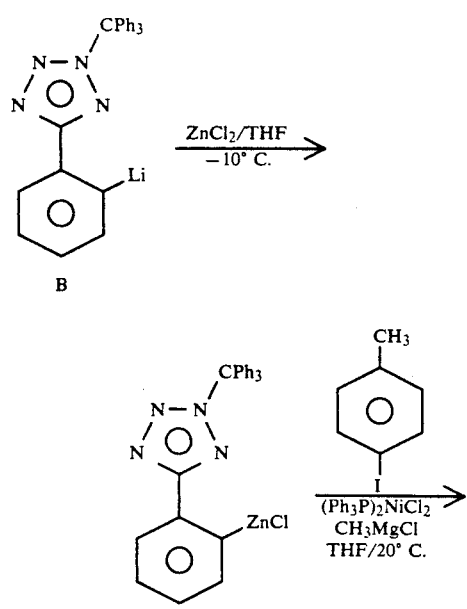

Scheme 3

EXAMPLE 1

1-(2-Trityltetrazol-5-yl)-2-(4-tolyl)benzene (2-Trityltetrazol-5-yl)benzene (25.0 g) was dissolved in dry THF (250 mL) and the solution of the tetrazole was cooled to −20° C. and n-butyllithium (28.3 mL, 2.5M in hexanes) was added. The mixture was gradually warmed to −10° C. over 1 hour and then aged at this temperature for an additional 30 minutes. A 1.4M THF solution of zinc chloride (51.3 mL) was then added to the aryllithium reagent prepared above while maintaining the lithium reagent solution at ≦0° C. In another flask an activated nickel catalyst solution was prepared as follows. To a solution of $(PPh_3)_2NiCl_2$ (2.5 g) in THF (35 mL) at 0° C. was added methylmagnesium chloride (2.5 mL, 3M in THF) followed by p-iodotoluene (17.5 g). The catalyst solution was warmed to 20° C. and the solution of the zinc reagent was added at a rate that maintained the reaction temperature between 20° to 25° C. Ten hours after the addition of the zinc reagent to the reaction was complete, the reaction mixture was cooled to 0° C., 8.0 g of SuperCel (filter aid) was added, followed by the addition of concentrated ammonium hydroxide (15 mL) over 30 minutes. The heterogeneous solution was aged at 0° C. for 1 hour and filtered. The filter cake was washed with THF (50 mL). The filtrate was washed with a mixture of saturated NaCl (80 mL) and saturated NaHCO₃ (30 mL) and the layers separated. The THF layer was dried with anhydrous Na₂CO₃ (30 g) and filtered. The volume of the filtrate was reduced to 150 mL and cyclohexane (300 mL) was added. The THF was further distilled in vacuo while the temperature of the mixture was maintained at 40° to 45° C. Cyclohexane was added periodically to maintain the volume at 200 mL. When the amount of THF dropped to ≦3 percent, the distillation was stopped and the mixture was cooled to room temperature. Hexanes (150 mL) was then added and the mixture further aged at 0° C. for 1 hour. The product was collected and washed with hexanes (100 mL). The yield was 28.8 g (94%).

EXAMPLES 2-12

Employing the procedures substantially as described in Example 1, but substituting an equivalent amount of reagent E₂ depicted in Table I for 4-iodotoluene to prepare 2-substituted 1-(tetrazol-5-yl)benzenes, also depicted in Table I.

TABLE I

[Reaction scheme: 1-(tetrazol-5-yl)benzene with R¹ substituent, treated with (1) n-BuLi, −10° C., THF; (2) ZnCl₂, THF, 0° C.; (3) E₂, (PPh₃)₂NiCl₂, CH₃MgCl, to give ortho-R⁴ substituted product]

| EX # | E₂ | R¹ | R⁴ |
|---|---|---|---|
| 2 | phenyl iodide | t-butyl | phenyl |
| 3 | o-iodotoluene | hydrogen | o-tolyl |
| 4 | m-iodotoluene | hydrogen | m-tolyl |
| 5 | p-iodotoluene | phenoxy | p-tolyl |
| 6 | p-iodoanisole | hydrogen | p-anisyl |
| 7 | 3-cyano-1-iodobenzene | hydrogen | m-cyanophenyl |
| 8 | 4-cyano-1-iodobenzene | hydrogen | p-cyanophenyl |
| 9 | 1-iodo-2,4-diethylbenzene | t-butyl | 2,4-diethylphenyl |
| 10 | 3-ethoxy-1-iodobenzene | hydrogen | m-ethoxyphenyl |
| 11 | methyl 4-iodobenzoate | phenyl | 4-methoxycarbonylphenyl |
| 12 | methyl 3-iodobenzoate | phenyl | 3-methoxycarbonylphenyl |

EXAMPLE 13

2-Bromo-1-(tetrazol-5-yl)benzene

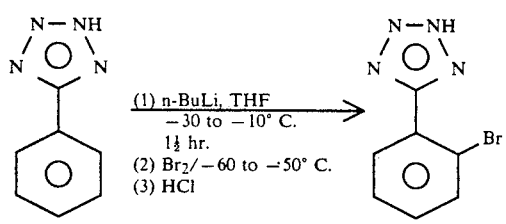

To (tetrazol-5-yl)benzene (0.29 g) in THF (10 ml) at −25° C. was slowly added n-butyllithium (2 mL, 2.5M in hexanes) while maintaining the reaction temperature below −15° C. When the addition was over in 10 to 15 minutes, the mixture was aged at −10° C. for 30 minutes. The reaction mixture was cooled to −60° C. and bromine (0.2 mL) was added dropwise. To the reaction mixture was added aqueous 10% sodium sulfite (5 mL). An HPLC assay showed a starting material/products ratio of 3.5/96.5. The product was precipitated by the addition of water (20 mL) and acidification with 2N HCl to pH 2. The mixture was aged at 0° C. for 1 hour and filtered. The yield was 0.427 g (95%).

EXAMPLES 14-24

Employing the procedures substantially as described in Example 13, but substituting for the bromine used therein an equivalent amount of reagent E₂ depicted in Table II there are prepared the ortho-substituted (tetrazol-5-yl)benzenes also depicted in Table II.

TABLE II

[Reaction scheme: trityl-protected 5-aryl-tetrazole with R¹ substituent, treated with (1) n-BuLi, THF, −30 to −10° C., 1½ hr.; (2) E₁, −78 to 25° C.; (3) HCl, giving ortho-R³ substituted product]

| EX # | E₁ | R¹ | R³ |
|---|---|---|---|
| 14 | benzaldehyde | t-butyl | α-hydroxybenzyl |
| 15 | benzaldehyde | hydrogen | α-hydroxybenzyl |
| 16 | phenyl disulfide | phenyl | phenylthio |
| 17 | phenyl disulfide | t-butyl | phenylthio |
| 18 | ethylene oxide | hydrogen | 2-hydroxyethyl |
| 19 | ethylene oxide | phenyl | 2-hydroxyethyl |
| 20 | carbon dioxide | phenoxy | carboxyl |
| 21 | carbon dioxide | phenyl | carboxyl |
| 22 | ethyl iodide | phenoxy | ethyl |
| 23 | butyl iodide | phenyl | butyl |
| 24 | tosyl azide | phenoxy | azide |

What is claimed is:

1. A process for the synthesis of a compound of structural formula:

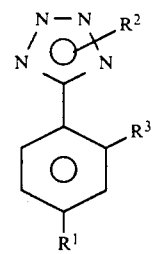

wherein:
R¹ is
  hydrogen,
  t-butyl,
  phenoxy,
  phenyl,
  di(C₁-C₆)-alkylamino, or
  trimethylsilyl; and
R² is
  hydrogen or
  trityl; and
R³ is
  α-hydroxybenzyl, trimethylsilyl,
thiophenyl,
thiomethyl,
carboxyl,
2-hydroxyethyl,
azido,
trimethylstannyl,
($C_1$–$C_6$)-alkyl,
bromo, or
iodo, respectively, and
which comprises treatment of an aryltetrazole, of structure:

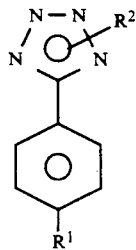

with an alkyllithium reagent in an aprotic solvent at a temperature range of between −40° to 10° C., for 0.5 to 5 hours, to give an ortho-lithiated intermediate, and reacting in situ with an appropriate electrophile, $E_1$, wherein:
  $E_1$ is
    benzaldehyde,
    trimethylsilyl chloride,
    phenyldisulfide,
    methyldisulfide,
    carbon dioxide,
    ethylene oxide,
    p-toluenesulfonyl azide,
    trimethylstannyl chloride,
    ($C_1$–$C_6$)-alkyl iodide,
    bromine, or
    iodine, respectively.

2. The process of claim 1, wherein $R^2$ is trityl.
3. The process of claim 1, wherein $R^1$ is hydrogen.
4. The process of claim 3, wherein the alkyllithium is straight or branched chain ($C_1$–$C_6$)alkyllithium.
5. The process of claim 2, wherein $R^1$ is hydrogen, $E_1$ is benzaldehyde, phenyldisulfide, carbon dioxide, ($C_1$–$C_6$)-alkyl iodide, bromine, or iodine and $R^3$ is α-hydroxybenzyl, phenylthio, carboxyl, ($C_1$–$C_6$)-alkyl, bromo, or iodo, respectively.
6. The process of claim 3, wherein $E_1$ is benzaldehyde, phenyldisulfide, ($C_1$–$C_6$)-alkyl iodide, carbon dioxide, bromine, or iodine; and $R^3$ is α-hydroxybenzyl, phenylthio, ($C_1$–$C_6$)-alkyl, carboxyl, bromo, or iodo, respectively.
7. The process of claim 3, wherein the aprotic solvent is tetrahydrofuran or diethyl ether.
8. The process of claim 3, wherein the alkyllithium is n-, s-, or t-butyllithium and the aprotic solvent is tetrahydrofuran, 2-methyltetrahydrofuran or diethyl ether.
9. The process of claim 6, wherein the alkyllithium is n-butyllithium and the aprotic solvent is tetrahydrofuran, 2-methyltetrahydrofuran or diethyl ether.
10. The process of claim 9, wherein the aprotic solvent is tetrahydrofuran or 2-methyltetrahydrofuran, the electrophile, $E_1$, is bromine, and $R^3$ is bromo.
11. A process for the preparation of a compound of structural formula:

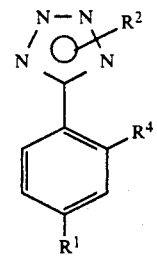

wherein:
  $R^1$ is
    hydrogen,
    t-butyl,
    phenoxy,
    phenyl,
    di($C_1$–$C_6$)-alkylamino, or
    trimethylsilyl; and
  $R^2$ is
    hydrogen, or
    trityl; and
  $R^4$ is
    α-hydroxybenzyl,
    α-hydroxy-($C_1$–$C_6$)-alkyl,
    ($C_1$–$C_6$)-alkyl,
    phenyl,
    o-, m-, or p-($C_1$–$C_6$)-alkylphenyl,
    o,p-di($C_1$–$C_6$)-alkylphenyl,
    o-, m- or p-($C_1$–$C_6$)-alkoxyphenyl,
    m- or p-biphenyl,
    o-, m- or p-cyanophenyl,
    m- or p-[carboxy-($C_1$–$C_6$)-alkyl]phenyl,
    m- or p-nitrophenyl,
    o-, m-, or p-chlorophenyl,
    bromide,
    iodide, or
    2-propen-1-yl
which comprises treatment of an aryltetrazole, of structure:

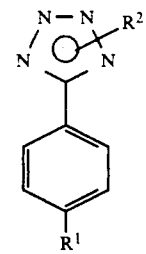

with an alkyllithium, in an aprotic solvent at a temperature range between −40° to 10° C. for 30 minutes to 5 hours, to give an ortho-lithiated intermediate followed by reaction with a metal halide, $M(L)_n$, in tetrahydrofuran or diethyl ether at −30° to 0° C., to give the transmetallated compound, wherein the metal (M) is selected from the group consisting of: Zn, Mg, Cu, B, Al, or Cd, and the ligand (L) is selected from the group consisting of: Cl, Br, or I and the number of ligands (n) corresponds to the valence on the metal, followed by reaction with an electrophile, $E_2$, wherein:
  $E_2$ is
    benzaldehyde,
    ($C_1$–$C_6$)-alkanal,
    ($C_1$–$C_6$)-alkyl halide, wherein the halide is Br, Cl, I, phenyl halide,
  o-, m-, or p-($C_1$–$C_6$)-alkylphenyl halide,
    o,p-di($C_1$–$C_6$)-alkylphenyl halide,
    m- or p-($C_1$–$C_6$)-alkoxylphenyl halide,
  o-, m- or p-halobiphenyl,
  o-, m- or p-cyanophenyl halide,
    m- or p-[carboxy-($C_1$–$C_6$)-alkyl]phenyl halide,
    m-, or p-nitrophenyl halide,
  o-, m-, or p-chlorophenyl halide, wherein the halide in the above aryl halide is Br or I,
bromine,
iodine, or
3-bromopropene, respectively,
either in the presence or absence of a phosphinated nickel or palladium catalyst which is activated, if necessary, by a Grignard reagent such as $CH_3MgCl$, PhMgCl, or diisobutylaluminum hydride ($R_2AlH$) in an aprotic solvent selected from the group consisting of: tetrahydrofuran, 2-methyltetrahydrofuran and diethyl ether at a reaction temperature of between −40° and 79° C. for a reaction time of between 0.5 and 16 hours to give the desired product.

12. The process of claim 11, wherein $R^2$ is trityl.
13. The process of claim 11, wherein $R^1$ is hydrogen.
14. The process of claim 12, wherein $R^1$ is hydrogen.
15. The process of claim 13, wherein the alkyllithium is straight or branched chain ($C_1$–$C_6$)-alkyllithium.
16. The process of claim 14, wherein the alkyllithium is straight or branched chain ($C_1$–$C_6$)-alkyllithium.
17. The process of claim 15, wherein the aprotic solvent is tetrahydrofuran or diethyl ether.
18. The process of claim 17, wherein the metal halide is $ZnCl_2$, $MgCl_2$, CuCl, $CuCl_2$ and the phosphinated nickel or palladium catalyst is $NiL_2(PPh_3)_2$, $PdL_2(PPh_3)_2$, or $Pd(PPh_3)_4$, wherein L is Cl, Br, I.
19. The process of claim 18, wherein $E_2$ is phenyl halide, o-, p- or m-($C_1$–$C_6$)-alkylphenyl halide, o,p-di($C_1$–$C_6$)-alkylphenyl halide, o-, m- or p-($C_1$–$C_6$)-alkoxyphenyl halide, m- or p-halobiphenyl, o-, m- or p-cyanophenyl halide, m- or p-carboxy-($C_1$–$C_6$)-alkylphenyl halide, m- or p-nitrophenyl halide, o-, m- or p-chlorophenyl halide, halide is define as bromide or iodide and $R^4$ is phenyl, o-, p- or m-($C_1$–$C_6$)-alkylphenyl, o,p-di($C_1$–$C_6$)-alkylphenyl, o-, m- or p-($C_1$–$C_6$)-alkoxyphenyl, m- or p-biphenyl, o-, m- or p-cyanophenyl, m- or p-carboxy-($C_1$–$C_6$)-alkylphenyl, m- or p-nitrophenyl, or o-, m- or p-chlorophenyl, respectively.
20. The process of claim 19, wherein $E_2$ is phenyl halide, o-, p- or m-($C_1$–$C_6$)-alkylphenyl halide, o,p-di($C_1$–$C_6$)-alkylphenyl halide, o-, m- or p-($C_1$–$C_6$)-alkoxyphenyl halide, 3- or 4-halobiphenyl, o-, m- or p-cyanophenyl halide, m- or p-carboxy-($C_1$–$C_6$)-alkylphenyl halide, wherein halide is defined as bromide or iodide, the metal halide is $ZnCl_2$, $MgCl_2$, or $CuCl_2$ and the phosphinated nickel or palladium catalyst is $NiCl_2(PPh_3)_2$, $PdCl_2(PPh_3)_2$, or $Pd(PPh_3)_4$, and $R^4$ is phenyl, o-, p- or m-($C_1$–$C_6$)-alkylphenyl, o,p-di($C_1$–$C_6$)-alkylphenyl, o-, m- or p-($C_1$–$C_6$)-alkoxyphenyl, 3- or 4-biphenyl, o-, m- or p-cyanophenyl, m- or p-carboxy-($C_1$–$C_6$)-alkylphenyl, respectively.
21. The process of claim 19, wherein the alkyllithium is n-, s-, or t-butyllithium.
22. The process of claim 20, wherein the alkyllithium is n-, s-, or t-butyllithium.
23. A process for the preparation of a compound of structural formula:

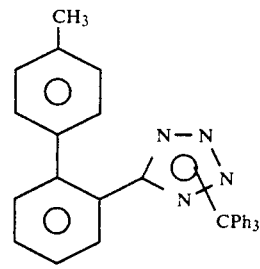

which comprises treating (2-trityltetrazol-5-yl)benzene

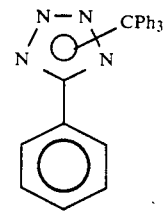

with n-butyllithium in tetrahydrofuran at −20° to −10° C., for 1½ to 2 hours, followed by a transmetallation of the lithiated species

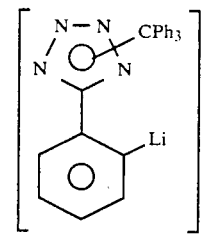

with zinc chloride in tetrahydrofuran at 0° C. and cross-coupling of the transmetallated species

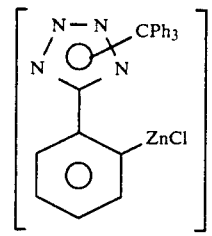

with 4-iodotoluene, in the presence of an activated phosphinated nickel catalyst which is derived from bis(triphenylphosphine)nickel(II) chloride and $CH_3MgCl$ in tetrahydrofuran at 20° C.

24. The process for the synthesis of the ortho-lithiated intermeidate of claim 1:

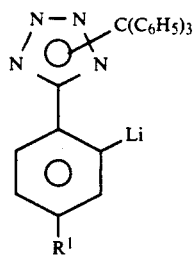

wherein:

R[1] is:

hydrogen, t-butyl, phenoxy, phenyl, di($C_1$–$C_6$)-alkylamino, or trimethylsilyl, and which comprises treatment of an aryltetrazole, of structure:

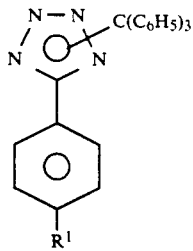

with an alkyllithium reagent in an aprotic solvent at a temperature range of between −40° to 10° C. for 0.5 to 5 hours.

25. The process for the synthesis of the ortho-lithiated intermediate of claim 1:

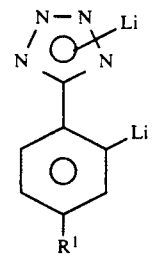

wherein:
R[1] is:
hydrogen,
t-butyl,
phenoxy,
phenyl,
di($C_1$–$C_6$)-alkylamino, or
trimethylsilyl, and which comprises treatment of an aryltetrazole, of structure:

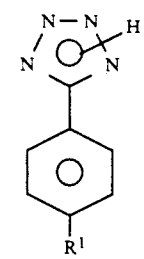

with an alkyllithium reagent in an aprotic solvent at a temperature range of between −40° to 10° C. for 0.5 to 5 hours.

26. A compound of structural formula:

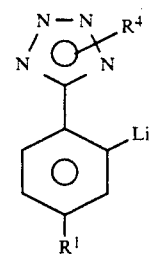

wherein:
R[1] is:
hydrogen,
t-butyl,
phenoxy,
phenyl,
di($C_1$–$C_6$)-alkylamino, or
trimethylsilyl; and
R[4] is lithium or trityl.

* * * * *